(12) United States Patent
Vitiello et al.

(10) Patent No.: US 10,767,257 B2
(45) Date of Patent: Sep. 8, 2020

(54) METHOD FOR REMOVING A METAL DEPOSIT ARRANGED ON A SURFACE IN A CHAMBER

(71) Applicant: KOBUS SAS, Montbonnot-Saint-Martin (FR)

(72) Inventors: Julien Vitiello, Grenoble (FR); Fabien Piallat, Montbonnot-Saint Martin (FR)

(73) Assignee: Plasma-Therm LLC, St. Petersburg, FL (US)

( * ) Notice: Subject to any disclaimer, the term of this patent is extended or adjusted under 35 U.S.C. 154(b) by 34 days.

(21) Appl. No.: 16/070,491

(22) PCT Filed: Jan. 16, 2017

(86) PCT No.: PCT/EP2017/050760
§ 371 (c)(1),
(2) Date: Jul. 16, 2018

(87) PCT Pub. No.: WO2017/125335
PCT Pub. Date: Jul. 27, 2017

(65) Prior Publication Data
US 2019/0032199 A1     Jan. 31, 2019

(30) Foreign Application Priority Data

Jan. 19, 2016 (FR) ...................... 16 50407

(51) Int. Cl.
| | | |
|---|---|---|
| *C23C 14/56* | (2006.01) |
| *C23C 16/44* | (2006.01) |
| *C23G 5/00* | (2006.01) |
| *H01J 37/32* | (2006.01) |
| *C23F 1/12* | (2006.01) |
| *C11D 11/00* | (2006.01) |

(Continued)

(52) U.S. Cl.
CPC ............ *C23C 14/564* (2013.01); *C07C 45/00* (2013.01); *C11D 11/0047* (2013.01); *C23C 16/4405* (2013.01); *C23F 1/12* (2013.01); *C23G 5/00* (2013.01); *H01J 37/32862* (2013.01); *C23C 16/45525* (2013.01)

(58) Field of Classification Search
None
See application file for complete search history.

(56) References Cited

U.S. PATENT DOCUMENTS

| | | |
|---|---|---|
| 2001/0009154 A1 | 7/2001 | Nguyen et al. |
| 2001/0034123 A1 | 10/2001 | Jeon et al. |
| 2004/0048461 A1 | 3/2004 | Chen et al. |

(Continued)

FOREIGN PATENT DOCUMENTS

| | | |
|---|---|---|
| WO | 2003008663 | 1/2003 |
| WO | 2006088284 | 8/2006 |
| WO | 2009042713 | 4/2009 |

*Primary Examiner* — Eric W Golightly
(74) *Attorney, Agent, or Firm* — Burr & Forman LLP; Harvey S. Kauget

(57) ABSTRACT

The invention relates to a method for removing a metal deposit (2) arranged on a surface (5) in a chamber (1), said method including repeatedly performing a sequence including: a) a first phase of injecting chemical species suitable for oxidizing said metal deposit (2); and b) a second phase of injecting chemical species suitable for volatilizing the oxidized metal deposit, said second phase b) being performed after the first phase a).

15 Claims, 2 Drawing Sheets

(51) Int. Cl.
*C07C 45/00* (2006.01)
*C23C 16/455* (2006.01)

(56) References Cited

U.S. PATENT DOCUMENTS

2008/0242078 A1  10/2008  Sprey et al.
2011/0259366 A1* 10/2011  Sweeney ............... C23C 14/48
                                          134/10
2015/0255259 A1*  9/2015  Li ....................... H01J 37/32091
                                          134/18

* cited by examiner

Prior Art

METHOD FOR REMOVING A METAL DEPOSIT ARRANGED ON A SURFACE IN A CHAMBER

FIELD OF THE INVENTION

The present invention relates to a method for removing a metal deposit arranged on a surface in a chamber.

BACKGROUND OF THE INVENTION

A method for removing a metal deposit from a surface in a chamber known from the state of the art includes the following steps:
  a) a step in which the metal deposit is oxidised;
  b) a step in which chemical species suitable for volatilising the oxidised metal deposit are injected, said second step b) being performed during at least part of step a).

However, the effectiveness of such a removal method remains to be improved.

The chemical species suitable for volatilising the oxidised metal deposit may also react with the metal deposit prior to its oxidation. This is how step a) may be blocked.

The reaction of the chemical species with the metal deposit may therefore interfere with the removal method and above all compromise its effectiveness.

This is particularly the case when the removal method is performed to remove a copper (Cu) deposit from a surface in a chamber. Step a) generally includes the introduction of gaseous oxygen or gaseous ozone. Chemical species suitable for volatilising copper oxide include hexafluoroacetylacetone (hfacH). The hfacH chemical species also reacts with the copper before it is oxidised when the former is injected into the chamber. The oxidation reaction is then blocked.

The purpose of the present invention is therefore to propose a method for removing a metal deposit that makes it possible to limit interfering reactions, which are likely to block said method.

A first application of the invention relates to the cleaning of metal residues arranged on the inner walls of a deposition chamber.

Another application of the invention relates to the manufacturing of printed circuits and, more specifically, the etching of metal layers used, among others, for filling vias, which are metallised holes establishing electrical connection between several layers of a printed circuit.

Conventionally, the vias are filled in excess with a metal such as copper, so as to ensure satisfactory filling of the vias. The excess metal is removed by a chemomechanical etching step. A stop layer is arranged between the printed circuit substrate and the metal deposition layer to control the etching thickness. The chemomechanical etching step requires the use of stop layers to ensure very precise control of the method and further requires subsequent operations consisting in cleaning the etched surface, which is complex and expensive.

Another purpose of the invention is to propose a simplified and less expensive method for manufacturing metallised vias.

BRIEF DESCRIPTION OF THE INVENTION

The present invention aims to overcome all or part of the aforementioned drawbacks and relates to a method for removing a metal deposit arranged on a surface in a chamber, said method including repeatedly performing a sequence including the following:
  a) a first phase of injecting chemical species suitable for oxidising said metal deposit;
  b) a second phase of injecting chemical species suitable for volatilising the oxidised metal deposit, said second phase b) being performed after the first phase a).

The injection of the chemical species suitable for volatilising the oxidised metal deposit after the injection of the chemical species suitable for oxidising the metal deposit thus makes it possible to avoid, on the one hand, a reaction of said species with each other and, on the other hand, an interfering reaction, including the reaction of the metal deposit arranged on a surface in a chamber with said chemical species.

Moreover, injecting, in the form of one or several pulses, the chemical species suitable for oxidising the metal deposit and for volatilising the oxidised metal deposit also makes it possible to limit the quantity of said chemical species.

According to one method of implementation, in phase b), the chemical species are injected in a substoichiometric quantity with respect to the quantity of the metal deposit oxidised in phase a).

The consumption of chemical species suitable for volatilising the oxidised metal deposit can thus be limited and, therefore, the cost of removing the deposit can be limited.

According to one embodiment, the sequence includes a phase between phase a) and phase b) during which no chemical species is injected into the chamber.

Moreover, the sequence may include an at least partial chamber purging phase between phase a) and phase b).

Furthermore, the method may include, between two consecutive sequences, a step in which no chemical species is injected into the chamber and/or the chamber is at least partially purged.

According to one method of implementation, the chamber is maintained at a temperature between 20 and 250° C., preferably between 20 and 150° C.

According to one method of implementation, step a) is performed by injecting an oxidising species comprising at least one of the following species: oxygen, ozone, nitrous oxide.

According to one method of implementation, the chemical species injected in step b) include hexafluoroacetylacetone.

Particularly advantageously, the chemical species injected in phase a) and/or in phase b) can be plasma-activated.

According to one method of implementation, the metal deposit includes at least one of the following elements: Copper, Titanium, Tantalum, Ruthenium, Zinc, Zirconium, Vanadium, Silver, Gold, Chromium.

Another purpose of the invention relates to a method of cleaning metal residues arranged on the inner walls of a deposition chamber, wherein said residues are removed using the removal method as described above.

Another purpose of the invention relates to a method for etching a metal deposit deposited in excess on a surface, wherein at least a portion of said metal deposit is removed by means of the removal method as described above.

According to one embodiment, prior to the first sequence of a) and b) phases, a mask is affixed on the metal deposit in a localised manner.

The etching method may then include the following steps:
  the mask is affixed to each area of the metal deposit that is to be preserved;

the sequence of a) and b) phases is performed one or several times to remove the excess metal deposit in each area not covered by the mask.

Alternatively, the etching method may include the following steps:
the mask is affixed to each area of the metal deposit that is to be etched;
chemical species suitable for passivating the metal deposit in each area not covered by the mask are injected;
the mask is removed;
the sequence of a) and b) phases is performed one or several times to remove the excess metal deposit in each area previously covered by the mask.

The sequence of a) and b) phases can be repeated as many times as necessary to remove the excess metal deposit.

BRIEF DESCRIPTION OF THE FIGURES

The invention will be better understood upon reading the following description of the specific although not restrictive embodiments of the invention while referring to the appended figures wherein.

DETAILED DESCRIPTION OF EMBODIMENTS OF THE INVENTION

For the sake of simplifying the description, the same references will be used for elements that are identical or which have the same function in the various methods of implementation.

Figure 1:
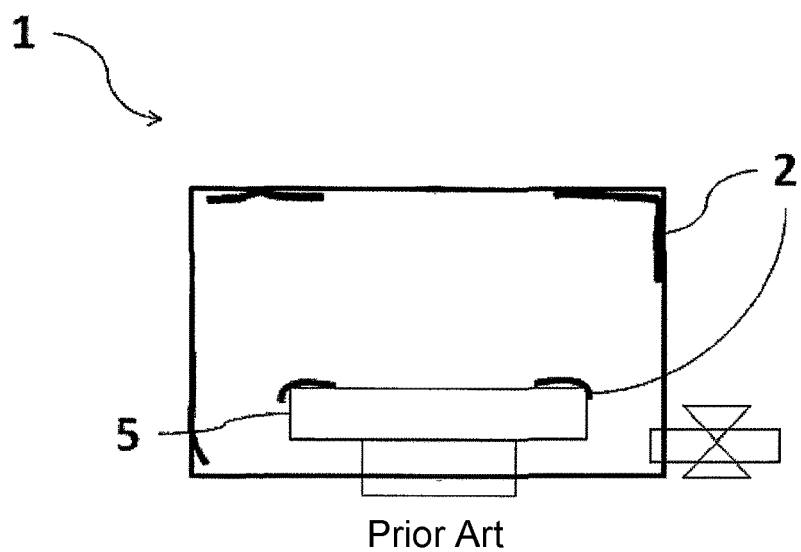
FIG. 1 is a schematic representation of a chamber.

FIG. 1 shows a chamber 1 in which a holder 5 is arranged.

An undesirable metal deposit 2 is observed on surfaces within the chamber 1, i.e. on the inner walls of the chamber 1, as well as on the holder 5.

The metal deposit 2 may include at least one of the following elements: Copper, Titanium, Tantalum, Ruthenium, Zinc, Zirconium, Vanadium, Silver, Gold, Chromium.

The method for removing the metal deposit 2 from the surfaces in the chamber 1 is performed cyclically, by repeating one or several sequences each including a first phase a) consisting in injecting into the chamber species that are suitable for oxidising the metal deposit and a second phase b) consisting in injecting into the chamber species that are suitable for volatilising the oxidised metal deposit, said second phase b) being performed after the end of the first phase a). In other words, this method avoids the simultaneous injection of species for oxidising the metal deposit and of species intended for volatilising the oxidised metal deposit. Phases a) and b) can optionally be separated by a given time period during which no species is injected into the chamber or during which the chamber is at least partially purged.

Phase a) can be performed by injecting oxidising species in gaseous form using an injection system (not shown).

Phase a) can be performed by injecting oxidising species including at least one of the following species: oxygen, ozone, nitrous oxide.

The oxidising species are injected in a pulsed manner (in the form of one or several pulses) during said first phase a) of the cleaning sequence.

According to some methods of implementation:
the duration of the pulse(s) for injecting oxidising species ranges from 0.02 s to 5 s, and the delay between two consecutive pulses (if any) ranges from 0.02 s to 10 s;
the duration of the pulse(s) for injecting oxidising species ranges from 0.02 s to 1 s, and the delay between two consecutive pulses (if any) ranges from 0.02 s to 1 s;
the duration of the pulse(s) for injecting oxidising species ranges from 1 s to 5 s, and the delay between two consecutive pulses (if any) ranges from 1 s to 10 s.

When the oxidising species are injected, a reaction oxidising the metal deposit 2 occurs on its free surface.

The chemical species suitable for volatilising the oxidised metal deposit used in the second phase of the cleaning sequence could also react with the metal deposit 2 and thus passivate the exposed surface of said deposit. The reaction passivating the metal deposit 2 is an interfering reaction, which limits or blocks any reaction in which the oxidising species oxidise said deposit.

In order to avoid this interfering reaction, the chemical species suitable for volatilising the oxidised metal deposit are injected, in phase b) after the end of phase a), in a pulsed manner (in the form of one or several pulses), by an injection system (not shown).

According to some methods of implementation:
the duration of the pulse(s) for injecting oxidising chemical species suitable for volatilising the oxidised metal deposit ranges from 0.02 s to 5 s, and the delay between two consecutive pulses (if any) ranges from 0.02 s to 10 s;
the duration of the pulse(s) for injecting chemical species suitable for volatilising the oxidised metal deposit ranges from 0.02 s to 1 s and the delay between two consecutive pulses (if any) ranges from 0.02 s to 1 s;
the duration of the pulse(s) for injecting chemical species suitable for volatilising the oxidised metal deposit ranges from 1 s to 5 s, and the delay between two consecutive pulses (if any) ranges from 1 s to 10 s.

Figure 2A:
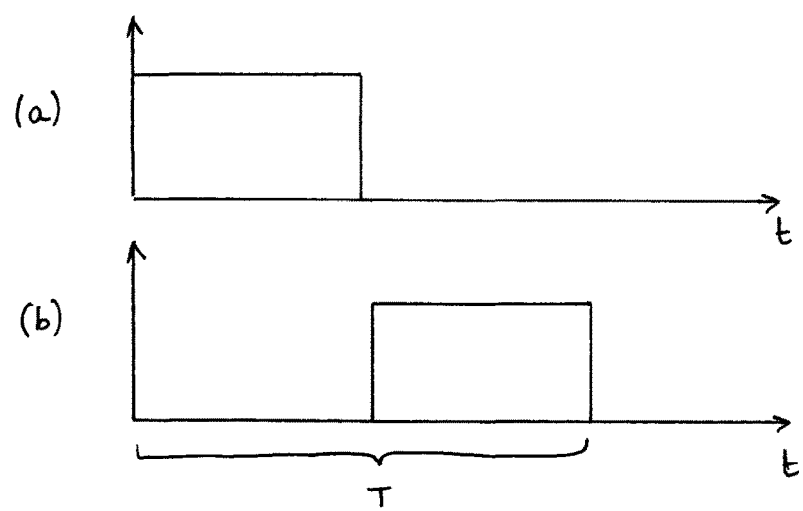
FIG. 2A shows, on graph (a), the quantity of oxidising species injected into the chamber as a function of time according to one embodiment of the invention and, on graph (b), the quantity of chemical species suitable for volatilising the oxidised metal deposit injected into the chamber as a function of time according to said embodiment of the invention, the time scale being the same as that of graph (a)
Figure 2B:
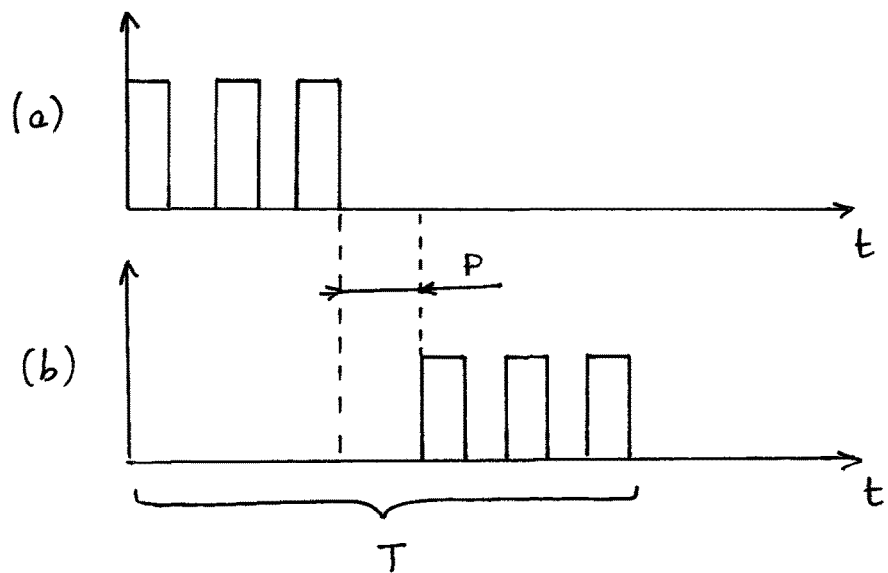
FIG. 2B shows, on graph (a), the quantity of oxidising species injected into the chamber as a function of time according to another embodiment of the invention and, on graph (b), the quantity of chemical species suitable for volatilising the oxidised metal deposit injected into the chamber as a function of time according to said embodiment of the invention, the time scale being the same as that of graph (a)

Although the pulses shown in FIGS. 2A and 2B have a strobe shape, other pulse shapes may be considered, if two successive pulses are separated by a time interval during which no chemical species suitable for oxidising the metal deposit or for volatilising the oxidised metal deposit is injected.

The chamber 1 can be maintained at a temperature ranging from 20 to 250° C. so as to maintain the chemical species suitable for volatilising the metal deposit in gaseous form. Preferably, the temperature of the chamber 1 is maintained at a temperature between 20 and 150° C. and, still preferably, between 20 and 100° C.

The pressure in the chamber 1 is maintained between 0.1 and 10 Torr or, preferably, between 1 and 5 Torr.

The method advantageously starts with phase a) of a first sequence in order to oxidise the metal deposit 2 at least on its free surface.

An oxidised metal deposit layer thus covers the metal deposit 2.

In a particularly advantageous manner, the oxidation kinetics of the metal deposit 2 are predetermined.

The oxidation kinetics of the metal deposit 2 depend on the nature thereof and on the conditions under which it is formed, but also on the oxidation conditions of phase a).

However, it is within the abilities of those skilled in the art to empirically determine the oxidation kinetics of the metal deposit 2.

In this regard, the skilled person can refer to the document Guangwen Zhou et al., J. Mater. Res., Vol. 20, No. 7 (1684-1694), July 2005.

Thus, prior to implementing the method for removing the metal deposit 2 from a surface in the chamber 1, it is advantageous to determine the oxidation kinetics of the metal deposit for various oxidation conditions and to draw charts for each of the metal deposit 2 types that are likely to be deposited on a surface within the chamber 1.

Said charts can then be used to determine the quantity of oxidised metal deposit for a predetermined duration and under given oxidation conditions.

Therefore, to implement the method for removing the metal deposit 2 from a surface in the chamber 1, the use of said charts makes it possible to determine the quantity of metal deposit oxidised in phase a) as a function of the duration of the pulse(s) and the flow rate of species injected during each pulse.

During each pulse of phase b), the oxidised metal deposition layer is, at least partly, volatilised by the chemical species.

Once the first sequence of phases a) and b) is complete, oxidising species are again injected into the chamber (new phase a)), so that said oxidising species are the majority in chamber 1 and, consequently, the reaction oxidising the metal deposit 2 is the dominant reaction, then a new phase b) is performed. Optionally, a purge of the chamber can be performed between phase b) of a sequence and phase a) of the following sequence and/or a period of time during which no species is injected into the chamber is observed between two consecutive sequences.

Advantageously, the duration of the pulse(s) of phase b) is adjusted so that the layer of the oxidised metal deposit is not completely volatilised. The part of the oxidised metal deposit layer that remains thus forms a barrier against the passivation of the metal deposit 2 by the chemical species injected in phase b). The passivation reaction is then avoided.

In other words, during the injection of the chemical species for volatilising the oxidised metal deposit in phase b), the chemical species are injected in a substoichiometric quantity with respect to the quantity of metal deposit oxidised in phase a) of the same sequence.

The aforementioned substoichiometric quantity can be determined when both the quantity of metal deposit oxidised in phase a) and the mechanism of the volatilisation reaction of said metal deposit oxidised with the chemical species are known.

In a particularly advantageous manner, the oxidising species and/or the species intended to volatilise the oxidised metal deposit are activated by a plasma source located in situ or at a distance from the chamber. Said species are thus more reactive and are therefore likely, even if the phases a) and/or b) are performed with short pulses, to reach all the surfaces of the chamber covered with the metal deposit to be removed.

The mode of injection of the chemical species suitable for oxidising the metal deposit and for volatilising the oxidised metal deposit thus has many advantages.

The first advantage is to make the removal method according to the invention effective. In fact, the interfering reaction, which includes the passivation of the metal deposit 2 by the injected chemical species, is thus neutralised. The neutralisation of said interfering reaction avoids having to open the chamber 1 and to use a process for decontaminating the latter.

The second advantage is to be able to control the quantity of chemical species injected during phases a) and b), and thus makes it possible to reduce the cost of the removal method.

Examples of Implementation

By way of example, phase a) is performed by injecting oxygen according to a pulse of a duration ranging from 100 ms to 1,000 ms, preferably from 100 ms to 500 ms, e.g. 200 ms, with a flow rate ranging from 100 to 1,000 sccm (standard cubic centimetres per minute), preferably from 100 to 500 sccm, e.g. 300 sccm.

The chemical species suitable for volatilising the oxidised metal deposit may include hexafluoroacetylacetone (hfacH).

The hfacH species are injected in phase b) according to a pulse whose duration ranges from 100 ms to 1,000 ms, preferably from 100 ms to 500 ms, e.g. 200 ms, with a flow rate ranging from 10 to 500 mg·min$^{-1}$ (milligrams per minute), preferably between 10 and 100 mg·min$^{-1}$, e.g. 50 mg·min$^{-1}$.

The temperature in the deposition chamber is maintained at 50° C.

Thus, when the metal deposit 2 includes copper (Cu), the oxidation reactions of phase a) are as follows:

$$2Cu+O_2 \rightarrow 2CuO$$

$$4Cu+O_2 \rightarrow 2Cu_2O$$

The oxidation of phase a) ceases in phase b) and the oxidised metal deposit is volatilised by the hfacH species injected according to the following reactions:

$$2H+2hfacH+CuO \rightarrow Cu(hfacR)_2+H_2O$$

$$2H+2hfacH+Cu_2OCu+Cu(hfacR)_2+H_2O$$

FIG. 2A illustrates an embodiment of a sequence of a) and b) phases, showing the flow rate of species injected into each of said phases over time t. In this embodiment, phase a) consists of a single pulse for injecting the oxidising species (e.g. an oxygen plasma (O2)). Phase b) immediately follows phase a) and consists of a single pulse for injecting the species intended to volatilise the oxidised copper deposit (e.g. an hfacH plasma). T specifies the duration of the sequence. In the particular case illustrated, the duration of phase a) is substantially equal to the duration of phase b), and is for example of the order of 500 ms. However, this value as well as the relative duration of phases a) and b) are purely indicative and may vary according to the flow rate of the injected species and to the oxidation and volatilisation kinematics.

FIG. 2B illustrates an embodiment of a sequence of a) and b) phases, showing the flow rate of species injected into each of said phases over time t. In this embodiment, phase a) consists of a series of three pulses for injecting the oxidising species (e.g. an oxygen plasma), said pulses being separated by a time interval during which a vacuum is established in the chamber. A period of time is allowed between the end of the last pulse of phase a) and the first pulse of phase b), this period of time, referred to as P, possibly being used to purge the chamber. Phase b) consists of a series of three pulses for injecting the species intended to volatilise the oxidised copper deposit (e.g. an hfacH plasma). T specifies the duration of the sequence. In the particular case illustrated, the duration of phase a) is substantially equal to the duration of phase b) and is for example of the order of 1.5 s. However, these values, as well as the relative duration of phases a) and b) and the number of pulses performed in each phase, are purely indicative and may vary according to the flow rate of the injected species and the oxidation and volatilisation kinematics.

Compared to a method in which the oxygen plasma is continuously injected and the hfacH plasma is injected in pulses without interrupting the injection of the oxygen plasma, with a method according to the invention, faster removal of the copper deposit can be observed visually.

Applications

The following description introduces two applications in which the removal method is implemented. The characteristics described above with reference to the removal method can be transposed to these two applications.

In a first application of the invention, the removal method is implemented to clean metal residues 2 arranged on the inner walls of a deposition chamber 1.

In this first embodiment, the chamber mentioned in the removal method is a deposition chamber 1. The deposition chamber may be a chemical vapour deposition (CVD), physical vapour deposition (PVD), plasma-enhanced physical vapour deposition (PEPVD), atomic layer deposition (ALD) chamber.

When depositing a film on a substrate arranged on the holder 5 of the deposition chamber 1, undesirable deposits of the material included in the film are observed on surfaces in the deposition chamber 1, i.e. on the inner walls of the deposition chamber 1, as well as on the holder 5.

As successive deposits are performed in the chamber 1, said undesirable material deposits accumulate on these surfaces and are a source of significant contamination of the films formed on the substrates.

The films formed in these deposition chambers may be metal films and the material deposits included in said films observed on the inner walls of the deposition chamber 1 are called metal residues 2.

The invention then consists in cleaning these metal residues 2 arranged on the inner walls of the deposition chamber 1. In a manner analogous to the method for removing a metal deposit described above, the method according to the first embodiment includes the repetition of one or several sequences each including the following:
  a) a phase of injecting chemical species suitable for oxidising the metal residues 2;
  b) a phase of injecting chemical species suitable for volatilising the oxidised metal residues.

Phase b) is performed after phase a).

Figure 3:
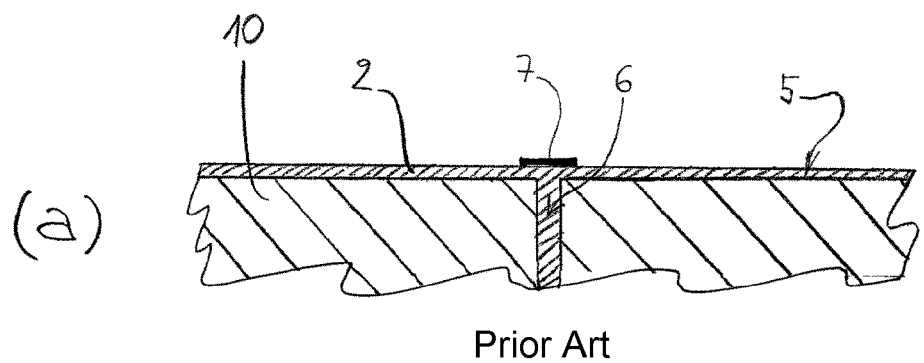
FIGS. 3(*a*) and 3(*b*) are partial cross-sections of a printed circuit, the method of the invention being implemented according to two variants for etching a metal deposit deposited in excess on the surface of a printed circuit substrate.
Figure 3:
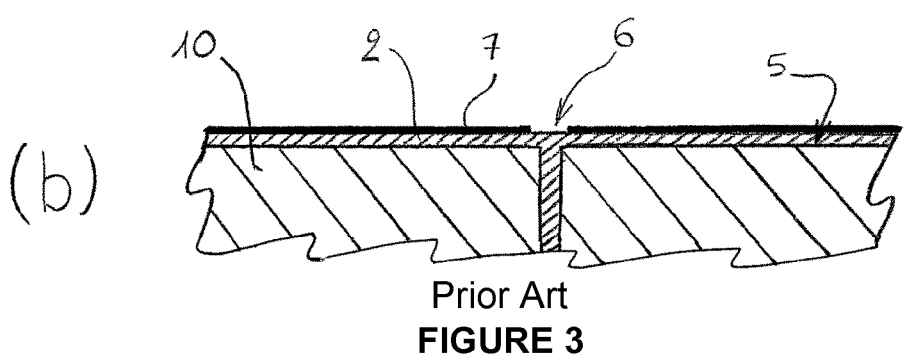

FIGS. 3(a) and 3(b) show two variants of a second application of the invention, wherein the method for removing a metal deposit 2 is used to manufacture a printed circuit 10, in order to etch a metal deposit 2 deposited on a substrate of the printed circuit.

In the example shown in FIGS. 3(a) and 3(b), the metal deposit 2 is used to fill a via 6. Vias 6 are metallised holes establishing the electrical connection between one or several layers of a printed circuit substrate.

In FIGS. 3(a) and 3(b), only one via 6 is shown, it being understood that the printed circuit 10 may comprise several vias 6.

The method of the invention can also be implemented in a more general way to etch a metal deposit deposited on the surface of a substrate. For example, the method allows for a pad to be produced on a printed circuit substrate, based on a metal deposit layer.

The printed circuit substrate 10 shown in FIGS. 3(a) and 3(b) has a face 5. A via 6 at least partially passes through the printed circuit 10 to electrically connect the face 5 to another layer (not shown) of the printed circuit 10.

The metal deposit 2 made is excessive. It fills the via 6 in order to metallise it in a satisfactory manner and also covers the face 5 of the printed circuit 10. The method of the invention can be used to etch this excessive metal deposit 2, so that the metal deposit only remains inside the via 6 and possibly extends outside along its longitudinal axis. Around the via 6 and on the surface 5, the metal deposit 2 is removed using the method of the invention.

The printed circuit 10 is placed in a chamber (not shown), for example a deposition chamber similar to the deposition chamber 1 described with reference to the first application of the method of the invention, to clean the metal residues.

FIG. 3(a) shows a first variant of the second embodiment. Prior to the implementation of the method, a mask 7 is affixed to each area of the metal deposit 2 to be preserved at the surface 5 of the printed circuit 10. The mask 7 is centred on the longitudinal axis of the via 6.

Then, the sequence of a) and b) phases of the method is performed one or several times in accordance with the invention to remove the excess metal deposit 2 from each area of the surface 5 not covered by the mask 7.

In phase a), the metal deposit 2 is oxidised only around the via 6, since the mask 7 protects the via 6. At the end of phase a), the part of the metal deposit 2 located in the via 6 and along its longitudinal axis is not oxidised.

In phase b), which is performed after phase a), chemical species suitable for volatilising the oxidised metal deposit 2 are injected into the chamber 1. In phase b), the chemical species are injected in a sequence of pulses.

The chemical species suitable for volatilising the oxidised metal deposit 2 only act around the via 6, as the mask 7 protects the metal deposit 2 at the via 6.

The sequence of a) and b) phases is repeated as many times as necessary to gradually remove the thickness of the part of the metal deposit 2 that is in excess.

FIG. 3(b) shows a second variant of the second embodiment. Prior to implementing the method, a mask 7 is affixed to each area of the metal deposit 2 to be etched at the surface 5 of the printed circuit 10 and around the via 6.

Chemical species suitable for passivating the metal deposit in each area not covered by the mask are then injected into the chamber 1. The passivation can be performed by injecting, in excess with respect to the quantity of the metal deposit, the oxidising species and/or the chemical species suitable for volatilising the oxidised metal deposit 2, preferably in a suprastoichiometric quantity with respect to the quantity of the metal deposit 2.

The metal deposit 2 is thus only passivated at the level of the unmasked areas, i.e. at the via 6.

The mask 7 is then removed.

The sequence of a) and b) phases of the method is then performed one or several times in accordance with the invention to remove the excess metal deposit 2 from the surface 5 in each area previously covered by the mask.

In phase a), the metal deposit 2 is only oxidised around the via 6, since at the level of the via 6, the metal deposit is passivated and thus fulfils the function of a mask. At the end of phase a), the metal deposit is not oxidised at the via 6.

In phase b), which is performed after phase a), chemical species suitable for volatilising the oxidised metal deposit 2 are injected into the chamber 1. In phase b), the chemical species are injected in a sequence of pulses.

The chemical species suitable for volatilising the oxidised metal deposit 2 only act around the via 6, as the passivation protects the metal deposit 2 at the via 6, as a mask would.

The sequence of a) and b) phases is repeated as many times as necessary to remove the excess metal deposit 2.

Compared to the conventional method of etching a metal deposit using chemical-mechanical polishing, the invention has the following advantages:

- While chemical-mechanical polishing requires the deposition of a thick metal layer (typically greater than or equal to 1.5 µm) to ensure the uniformity of the subsequent polishing, the etching performed in the invention makes it possible to only deposit the thickness of metal that is sufficient for filling the via, i.e. a few hundred nanometres deposited in excess. The invention thus makes it possible to reduce the amount of metal to be deposited by a factor of about 10.
- By avoiding the chemical-mechanical polishing which causes a significant contamination of the substrate, the invention also avoids the required cleaning steps following this polishing.
- Finally, the formation of a stop layer between the substrate and the metal deposit is no longer necessary.

Thus, owing to the invention, etching a metal deposit deposited on a surface is simpler and less expensive.

Of course, the invention is not limited to the methods of implementation described. Alternative embodiments can be provided without departing from the scope of the invention.

The method for removing a metal deposit according to the invention makes it possible to limit the interfering reactions that are likely to block said method.

REFERENCES

G. Zhou et al.: Initial oxidation kinetics of Cu(100), (110), and (111) thin films investigated by in situ UHV TEM, J. Mater. Res., Vol. 20, No. 7, July 2005

The invention claimed is:

1. A method for removing a metal deposit arranged on a surface in a chamber, said method including repeatedly performing a sequence including the following:
   a) a first phase of injecting chemical species suitable for oxidizing said metal deposit, first phase
      said injection of chemical species suitable for oxidizing said metal deposit being done in the form of one or several pulses;
   b) a second phase of injecting chemical species suitable for volatilizing the oxidized metal deposit, said second phase b) being performed after an end of the first phase a), second phase
      said injection of chemical species suitable for volatilizing the oxidized metal deposit being done in the form of one or several pulses; and
   adjusting the duration of the one or several pulses in phase b) to form a barrier against a passivation on the metal deposit, so that a layer of the oxidized metal deposit is not fully volatilized.

2. The method according to claim 1, wherein during each pulse in phase b), the oxidized metal deposit is at least partially volatilized by the chemical species.

3. The method according to claim 2, wherein the duration of the injection pulses ranges from 0.02 s to 5 s, and the delay between two consecutive pulses, if any, ranges from 0.02 s to 10 s.

4. The method according to claim 1, wherein the sequence includes a phase between phase a) and phase b) during which no chemical species is injected into the chamber.

5. The method according to claim 1, wherein the sequence includes an at least partial chamber purging phase between phase a) and phase b).

6. The method according to claim 1, including, between two consecutive sequences, a step in which no chemical species is injected into the chamber and/or the chamber is at least partially purged.

7. The method according to claim 1, wherein the chamber is maintained at a temperature between 20 and 250° C.

8. The method according to claim 1, wherein phase a) includes the injection of at least one of the following oxidizing species: oxygen, ozone, and nitrous oxide.

9. The method according to claim 1, wherein the chemical species injected in phase b) include hexafluoroacetylacetone.

10. The method according to claim 1, wherein the chemical species injected in phase a) and/or in phase b) are plasma-activated.

11. A method for cleaning metal residues arranged on the inner walls of a chemical vapour deposition chamber, wherein said metal residues are removed using the method of claim 1.

12. A method for etching a metal deposit deposited in excess on a surface, wherein at least a portion of said metal deposit is removed by means of the method of claim 1.

13. The method according to claim 12, characterized in that prior to the first sequence of a) and b) phases, a mask is affixed on the metal deposit in a localized manner.

14. The method according to claim 13, characterized in that it includes the following steps:
   the mask is affixed to each area of the metal deposit that is to be preserved;
   the sequence of a) and b) phases is performed one or several times to remove the excess metal deposit in each area not covered by the mask.

15. The method according to claim 1, characterized in that the sequence of a) and b) phases is repeated as many times as necessary to remove the excess metal deposit.

* * * * *